US012806417B2

(12) United States Patent
Song et al.

(10) Patent No.: US 12,806,417 B2
(45) Date of Patent: Nov. 24, 2026

(54) METHOD FOR CONTROLLING VAGUS NERVE STIMULATION

(71) Applicant: NEURIVE Co., Ltd., Gimhae-si (KR)

(72) Inventors: Jae Jun Song, Seoul (KR); Hyuk Choi, Seoul (KR); Ki Hwan Hong, Seoul (KR)

(73) Assignee: NEURIVE CO., LTD., Gimhae-si (KR)

( * ) Notice: Subject to any disclaimer, the term of this patent is extended or adjusted under 35 U.S.C. 154(b) by 211 days.

(21) Appl. No.: 18/568,912

(22) PCT Filed: Nov. 23, 2022

(86) PCT No.: PCT/KR2022/018647

§ 371 (c)(1),
(2) Date: Dec. 11, 2023

(87) PCT Pub. No.: WO2023/096359

PCT Pub. Date: Jun. 1, 2023

(65) Prior Publication Data

US 2024/0374896 A1 Nov. 14, 2024

(30) Foreign Application Priority Data

Nov. 26, 2021 (KR) ........................ 10-2021-0165567

(51) Int. Cl.
*A61N 1/36* (2006.01)
*A61N 1/04* (2006.01)

(52) U.S. Cl.
CPC ....... *A61N 1/36034* (2017.08); *A61N 1/0456* (2013.01)

(58) Field of Classification Search
CPC .... A61N 1/36034; A61N 1/0456; A61N 1/04; A61N 1/36; A61N 1/36053;
(Continued)

(56) References Cited

U.S. PATENT DOCUMENTS 9,415,220 B1 * 8/2016 Spinelli .............. A61N 1/36036
2007/0027504 A1 2/2007 Barrett et al.
(Continued)

FOREIGN PATENT DOCUMENTS

KR 10-0596540 B1 7/2006
KR 10-2019-0088300 A 7/2019
(Continued)

OTHER PUBLICATIONS

International Search Report issued on Feb. 27, 2023, for corresponding International Patent Application No. PCT/KR2022/018647, along with an English translation (6 pages).
(Continued)

*Primary Examiner* — Joseph A Stoklosa
(74) *Attorney, Agent, or Firm* — Hauptman Ham, LLP

(57) ABSTRACT

Proposed is a method for controlling vagus nerve stimulation to stimulate the vagus nerves in both ears, in which one or more of intensity (V), a frequency (F), and a pulse width (PW) of electrical stimulation that is applied to both vagus nerves are separately controlled, and the electrical stimulation that is applied to the vagus nerves in both ears is controlled such that a difference of E expressed by the following [Equation 1] becomes 5,000 or more, [Equation 1] $E=V^2\times F\times PW$. In this case, as units in the equation 1, the intensity is V, the frequency is Hz, and the pulse width is μs. There is an excellent effect that not only can improve an effect of vagus nerve stimulation, but also can activate the brain connected to the vagus nerve when stimulating the vagus nerve through electrodes being in contact with ears.

6 Claims, 2 Drawing Sheets

(58) Field of Classification Search
CPC .............. A61N 1/36025; A61N 1/3603; A61N 1/36036; A61M 21/00; A61M 21/02; A61M 2021/0072
See application file for complete search history.

(56) References Cited

U.S. PATENT DOCUMENTS

| | | | | |
|---|---|---|---|---|
| 2016/0271392 | A1 | 9/2016 | Vallejo et al. | |
| 2022/0233860 | A1* | 7/2022 | Hamner ............. | A61N 1/36031 |

FOREIGN PATENT DOCUMENTS

| | | | |
|---|---|---|---|
| KR | 10-2029914 | B1 | 10/2019 |
| WO | 2020/068830 | A1 | 4/2020 |

OTHER PUBLICATIONS

Written Opinion issued on Feb. 27, 2023, for corresponding International Patent Application No. PCT/KR2022/018647 (3 pages).

* cited by examiner

METHOD FOR CONTROLLING VAGUS NERVE STIMULATION

CROSS REFERENCE TO RELATED APPLICATION

The present application is a national stage filing under 35 U.S.C § 371 of PCT application number PCT/KR2022/018647 filed on Nov. 23, 2022, which is based upon and claims the benefit of priorities to Korean Patent Application No. 10-2021-0165567 filed on Nov. 26, 2021, in the Korean Intellectual Property Office. The disclosures of the aforementioned application are incorporated herein by reference in their entireties.

TECHNICAL FIELD

The present disclosure relates to a method of controlling stimulation to the vagus nerve and, more specifically, to a method of controlling stimulation, the method being able to increase the effect of vagus nerve stimulation and activate the brain.

BACKGROUND ART

The vagus nerve is one of cranial nerves and corresponds to the tenth cranial nerve. The vagus nerve is a mixed nerve combing out from the brain, distributed through the face, chest, and abdomen, and including parasympathetic nerve fibers and takes part in controlling of parasympathetic nerves acting on the heart, lungs, alimentary canal, etc. The vagus nerve has the longest and most complicated structure in the twelve pairs of cranial nerves and includes both of sensory nerve fibers and motor nerve fibers.

It has been known that vagus nerve stimulation devices for treating epilepsy and depression have been officially approved by FDA and these devices have cervical branches at the neck as an object. However, such electrical stimulation for the vagus nerve is a surgical procedure of exposing a cervical branch of the vagus nerve by directly cutting the skin, winding a coil that is an electrical corpuscle around the outside the cervical branch, and mounting a microchip, so it cannot be used in the field of self-treatment by ordinary people.

Vagus nerve stimulation devices for treating epilepsy and depression have an influence on the brain by controlling nerve signal going into the brain and are devices based on neuromodulation. Neuromodulation is a physiological process in which given neurons control various neuron groups using one or more chemical substances, and is different from synapse transmission of secreting a neurotransmitter at the ends of axons by aiming a fast acting receptor of one specific partner neuron. A method of supplying electrical stimulation or chemical stimulation to a nerve system is under study as a method for improving the function of a nerve system or reducing chronic pain using such neuromodulation. According to vagus nerve stimulation devices described above and deep brain stimulation devices, a device that applies electrical stimulation to a nerve is directly attached to a nerve inside a human body, so their application is very limited.

As method of directly applying an influence to the brain from the outside of a human body, there are magnetic stimulation in which a magnetic field applied from the outside of the head activates the brain and transcranial electrical stimulation in which electricity applied through an electrode attached to the cranium activates the cerebral cortex. Transcranial magnetic stimulation and transcranial electrical stimulation are non-invasive methods and have an effect of directly influencing the brain, but have limitation that the region of the brain that is stimulated is limited to the portion close to the cranium.

DISCLOSURE

Technical Problem

The present disclosure has been made in an effort to solve the problems described above and an objective of the present disclosure is to provide a method of controlling stimulation, the method having an effect of activating the brain when controlling stimulation that stimulates the vagus nerve.

Technical Solution

In order to achieve the objectives a method for controlling vagus nerve stimulation is a method for stimulating vagus nerves in both ears, in which one or more of intensity (V), a frequency (F), and a pulse width (PW) of electrical stimulation that is applied to both vagus nerves are separately controlled, and the electrical stimulation that is applied to the vagus nerves in both ears is controlled such that a difference of the values of E expressed by the following [Equation 1] becomes 5,000 or more, $$E = V^2 \times F \times PW \qquad \text{[Equation 1]}$$

where, as units in the equation 1, the intensity is V, the frequency is Hz, and the pulse width is μs.

The intensity (V) may be in a range of 3~80V.

The frequency (F) may be in a range of 10~120 Hz.

The pulse width (PW) may be in a range of 10~250 μs.

A difference of the frequency (F) may be 5 Hz or more.

The intensity (V) of electrical stimulation applied to an ear may be larger by 5% or more than smaller intensity (V) at the other ear.

- a ramp up time and a ramp down time may be applied in a range of 0.5~5 seconds when electrical stimulation is changed.

A device for stimulating the vagus nerve according to another aspect of the present disclosure includes: two electrodes configured to respectively apply electrical stimulation to vagus nerves positioned in both ears, respectively; and a controller configured to control one or more of intensity (V), a frequency (F), and a pulse width (PW) of electrical stimulation that is applied to the electrodes, in which the controller controls electrical stimulation that is applied to the vagus nerves in both ears such that a difference of E expressed by the following [Equation 1] becomes 5,000 or more, $$E = V2 \times F \times PW \qquad \text{[Equation 1]}$$

where, as units in the equation 1, the intensity is V, the frequency is Hz, and the pulse width is μs.

Advantageous Effects

The present disclosure configured as described above has an excellent effect that not only can improve an effect of vagus nerve stimulation, but also can activate the brain connected to the vagus nerve when stimulating the vagus nerve through electrodes being in contact with ears.

Further, since the method influences the deep portion of the brain connected with the vagus nerve, there is an effect that it is possible to activate the regions of the brain that could not be activated by transcranial magnetic stimulation and transcranial electrical stimulation that could influence only a portion of the cerebral cortex.

DESCRIPTION OF REFERENCE NUMERALS

Figure 1:
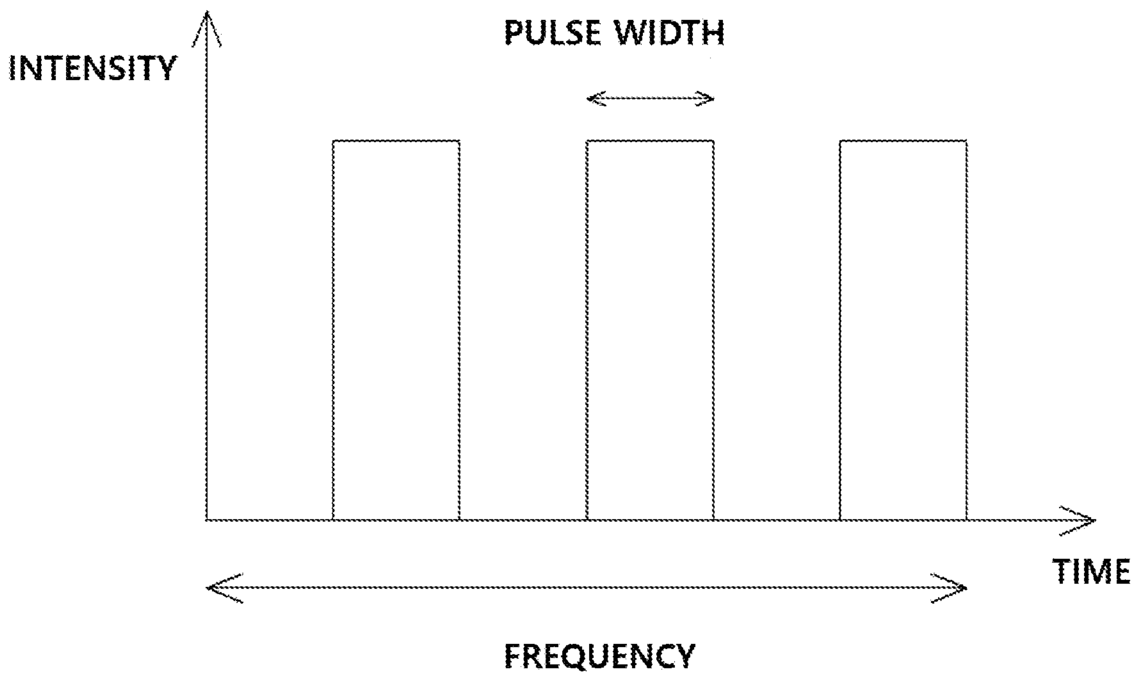
FIG. 1 is a diagram illustrating control elements for electrical stimulation that is applied to the vagus nerve.

10: vagus nerve stimulation device
100: left wearing part 110: electrode
200: right wearing part 210: electrode
300: controller

MODE FOR INVENTION

Embodiments of the present disclosure are described in detail with reference to the accompanying drawings.

However, such embodiments of the present disclosure may be modified in various ways and the scope of the present disclosure is not limited only to the embodiments to be described below. The shape, sizes, etc. of elements may be exaggerated in the drawings for clearer description and elements indicated by the same reference numerals in the drawings are the same components.

Further, when an element is referred to as being "connected with" another element throughout the specification, it may be "directly connected" to the other element and may also be "electrically connected" to the other element with another element intervening therebetween. Further, unless explicitly described otherwise, "comprising" or "having" any components will be understood to imply the inclusion of other components rather than the exclusion of any other components.

Terms "first", "second", etc. are provided for discriminating one component from another component and the scope of a right is not limited to the terms. For example, the first component may be named the second component, and vice versa.

FIG. 1 is a diagram illustrating control elements for electrical stimulation that is applied to the vagus nerve.

Electrical stimulation for stimulating the vagus nerve is controlled in a pulse wave type, and intensity V, a pulse width (PW), and frequency (F) can be controlled. In relation to electrical stimulation, the general term "frequency" and the unit Hz thereof are used only for an alternating current, and the term "pulse frequency" and pps (pulses per second) that is the unit thereof is used for a pulse current for discrimination, but the term "frequency" and Hz may be used for the pulse wave and are used in the specification.

In stimulation treatment using electrical stimulation, stimulation treatment is generally used in various types of treatment waves by controlling the intensity V, pulse width PW, and frequency F. Controlling such electrical stimulation is performed to adjust the intensity of stimulation that a user feels not to be excessively strong or weak and is performed also to increase the efficiency of stimulation by changing stimulation rather than continuously applying stimulation at a constant level.

When developing a neuromodulation technique for activating the brain function, the inventor(s) of the present disclosure has developed a neuromodulation technique using the vagus nerve unlike a transcranial magnetic stimulation method or a transcranial electrical stimulation method, and particularly, has developed a technique of activating the limbic system and the cerebral cortex through many central nuclei by stimulating the afferent sensory nerve by non-invasively stimulating the auricular vagus nerve.

Transcranial magnetic stimulation or transcranial electrical stimulation has the feature of stimulating the cerebral cortex, but the vagus nerve simulation according to the present disclosure is a technique that can effectively stimulate the brainstem and the deep brain by stimulating the deep portion of the brain through the vagus nerve that is the tenth cranial nerve.

The inventor(s) of the present disclosure has determined the phenomenon in which the brain is actively activated when different types of stimulation are applied to both ears in the process of stimulating the vagus nerves in both ears, and has derived first a reference that can quantify the influence on the brain by electrical stimulation that is applied to the vagus nerves in the ears in order to find out detailed conditions that induce activation of the brain.

In t case, the control range of electrical stimulation that can be applied to the vagus nerves in the ears is 3~80V for intensity (V), 10~120 Hz for frequency (F), and 10-250 μs for pulse width (PW). The control range of electrical stimulation was determined in consideration of the range of electrical stimulation that can be applied to the nerves of a human, the range that can be handled by non-specialists, etc.

It was possible to quantify the influence on the brain by electrical stimulation that is applied to the vagus nerve using E that is calculated from the following [Equation 1] and detailed condition that induce activation of the brain was derived on the basis of E.

$$E = V^2 \times F \times PW \qquad \text{[Equation 1]}$$

where, as the units in the equation, the intensity is V, the frequency is Hz, and the pulse width is μs.

Various studies have been conducted while changing electrical stimulation that is applied to the vagus nerves in both ears in the control range of electrical stimulation described above and it could be seen that activation of the brain is induced when the difference of E derived for electrical stimulation that is applied to both ears is 5,000 or more.

The vagus nerve is a path that transmits nerve signals between various organs and the brain of a human body, electrical stimulation to the vagus nerve is transmitted through the brain through nerve fibers, it has been generally known that electrical stimulation to the vagus nerve has an influence on the wide network of the brain. It has been known that when different types of electrical stimulation are applied to both ears, activation of the brain is induced by interaction of networks formed by different signals.

The method of stimulating the vagus nerve of the present disclosure is different from the function of vagus nerve stimulation devices that are installed on one vagus nerve stem and influence the brain by controlling nerve signals going into the brain. Further, unlike transcranial magnetic stimulation or transcranial electrical stimulation that activate the brain by influencing only a portion of the cerebral cortex, there is an effect that it is possible to activate the regions of the brain, which were not activated through transcranial magnetic stimulation or transcranial electrical stimulation, by influencing the deep portion of the brain connected with the vagus nerve.

In particular, it could be seen that activation of the brain is induced when the difference of frequencies (F) of electrical stimulation that is applied to the vagus nerves of both ear is 5 Hz.

Further, it could be seen that activation of the brain is induced even when the intensity of electrical stimulation applied to the vagus nerve in one of both ears is larger by 5% or more than the smaller intensity (V) at the vagus nerve in the other ear.

Since people feel uncomfortable or pain when electrical stimulation that is applied to an ear is excessively changed, it is better to apply a ramp up time and a ramp down time within the range of 0.5~5 seconds when changing electrical stimulation.

Meanwhile, sound stimulation may be applied with stimulation to the vagus nerve. It is possible to adjust activation of the cerebral cortex through sound stimulation and this effect can promote variation by influencing nerve synapses related to degenerative brain diseases on the basis of neural plasticity. The noninvasive vagus nerve stimulation of the present disclosure can improve neural plasticity of the cerebrum by stimulating the cerebral cortex through the nucleus tractus solitarius, locus coeruleus, and nucleus basalis, thereby being able to promote formation of new synapses and improve learning ability. Variation of cerebral synapses by sound stimulation induces synergy with improvement of cerebral plasticity by the noninvasive vagus nerve of the present disclosure, so it is possible to improve the effect of treatment.

Figure 2:
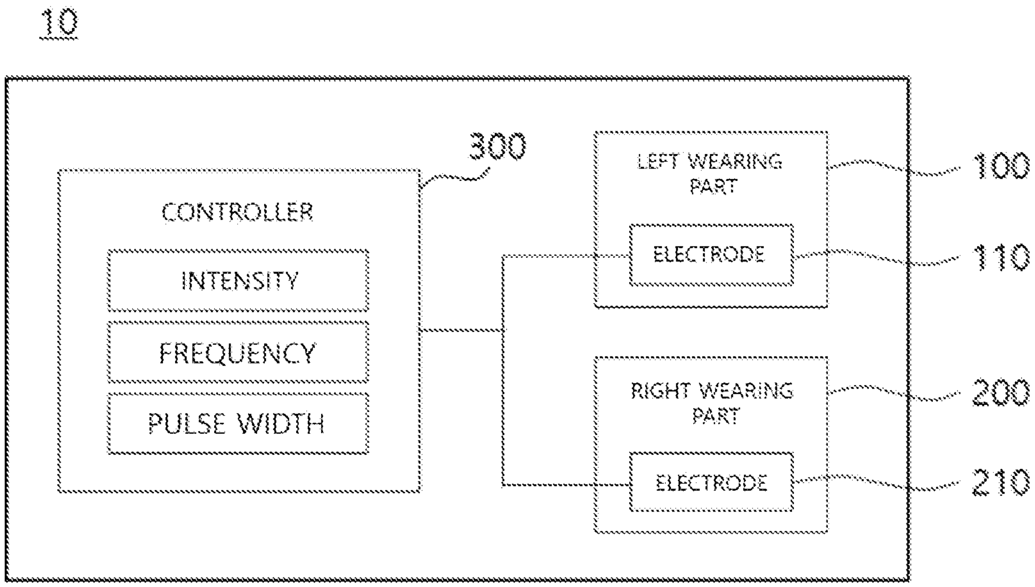
FIG. 2 is a diagram illustrating the configuration of a vagus nerve stimulation device according to an embodiment of the present disclosure.

FIG. 2 is a diagram illustrating the configuration of a vagus nerve stimulation device according to an embodiment of the present disclosure.

A vagus nerve stimulation device 10 of the present disclosure includes a left wearing part 100 that is worn on the left ear of a user and a right wearing part 200 that is worn on the right ear, in which electrode 110 and 210 for applying electrical stimulation to the vagus nerves of ears are formed respectively at the left wearing part 100 and the right wearing part 200.

The detailed structures of the left wearing part 100 and the right wearing part 200 may be applied in various ways without spoiling the features of the present disclosure. The left wearing part 100 and the right wearing part 200 may be separated and individually worn, and in this case, the structure for fixing the wearing parts to the ears of a user is also not limited. For example, the wearing parts may be fixed to ears by a structure that is inserted in the external auditory canal and may be fixed to ears by a separate fixing member such as an ear ring, and the shape of the fixing member can also be applied without limitation within the range that does not spoil the features of the present disclosure. The device may further include a connector structurally connect the left wearing part 100 and the right wearing part 200 and existing types can be applied for the structure of the connector without limitation such as the types that are supposed to be positioned on the head, the back of the neck, etc. Even though the connector is included, the left wearing part 100 and the right wearing part 200 can be fixed to the ears of a wearer by elasticity of the connector and may be fixed to ears by specific fixing members.

The detailed structures of the electrodes 110 and 120 of the left wearing part 100 and the right wearing part 200 may also be applied in various ways without spoiling the features of the present disclosure. In particular, the related art can be applied in various ways for the position and shape that come in contact with an ear to stimulate the vagus nerve, and representatively, the wearing parts may be formed to come in contact with the cymba concha of an ear or to be inserted in the external auditory canal in a contact state.

A controller 300, which is a component for controlling electrical stimulation that is applied to the vagus nerve through the electrode 110 and 120 of the left wearing part 100 and the right wearing part 200, is characterized in that it can separately control electrical stimulation that is applied to the electrode 110 of the left wearing part 100 and the electrode 210 of the right wearing part 200. The controller 300 can control the intensity (V), pulse width (PW), and frequency (F) of electrical stimulation.

The controller 300 controls electrical stimulation that is applied to the left electrode 110 and electrical stimulation that is applied to the right electrode 210 such that the difference of E calculated through the following [Equation] becomes 5,000 or more.

$$E = V^2 \times F \times PW \qquad \text{<Equation 1>}$$

where, as the units in the equation, the intensity is V, the frequency is Hz, and the pulse width is μs.

When different types of electrical stimulation are applied to the vagus nerves in both ears through control by the controller 300, interaction occurs between networks of the brain formed by different signals transmitted to the brain through the nerve fibers of the vagus nerves, so activation of the brain is induced.

The control range of electrical stimulation that is controlled by the controller 300 is set such that the intensity (V) is in the range of 3~80V, the frequency (F) is in the range of 10~120 Hz, and the pulse width (PW) is in the range of 10~250 μs.

In this case, the controller 300 can control the difference of frequencies (F) of the electrical stimulation that is applied to the vagus nerves of both ears to be 5 Hz or more. Further, the controller 300 can control the intensity of electrical stimulation that is applied to an ear to be larger by 5% or more than the smaller intensity (V) at the vagus nerve in the other ear.

Further, the t controller 300 can change electrical stimulation by applying a ramp up time and a ramp down time within the range of 0.5~5 seconds so that a wearer does not feel uncomfortable or pain in the process of changing electrical stimulation.

Exemplary embodiments of the present disclosure were described above, but it would be understood by those skilled in the art that these embodiments described above are only examples of the spirit of the present disclosure and the present disclosure may be changed in various ways without departing from the spirit of the present disclosure. Accordingly, the protective range of the present disclosure should be construed on the basis of claims rather than specific embodiments and all of spirits within the equivalent range should be construed as being included in the range of right of the present disclosure.

The invention claimed is:

1. A method for controlling vagus nerve stimulation to stimulate vagus nerves in both ears, wherein one or more of intensity (V), a frequency (F), and a pulse width (PW) of electrical stimulation that is applied to both vagus nerves are separately controlled, and the electrical stimulation that is applied to the vagus nerves in both ears is controlled such that a difference between a first value of E for a first ear and a second value of E for a second ear becomes 5,000 or more, wherein E is expressed by the following [Equation 1], $$E = V^2 \times F \times PW \qquad \text{[Equation 1]}$$

(where, as units in the equation 1, the intensity is V, the frequency is Hz, and the pulse width is μs), wherein a difference of the frequency (F) is 5 Hz or more, or wherein the intensity (V) of electrical stimulation applied to an ear is larger by 5% or more than smaller intensity (V) at the other ear.

2. The method of claim 1, wherein the intensity (V) is in a range of 3~80V.

3. The method of claim 1, wherein the frequency (F) is in a range of 10~120 Hz.

4. The method of claim 1, wherein the pulse width (PW) is in a range of 10~250 μs.

5. The method of claim 1, wherein a ramp up time and a ramp down time are applied in a range of 0.5~5 seconds when electrical stimulation is changed.

6. A device for stimulating the vagus nerve, comprising:

two electrodes configured to respectively apply electrical stimulation to vagus nerves positioned in both ears, respectively; and a controller configured to control one or more of intensity (V), a frequency (F), and a pulse width (PW) of electrical stimulation that is applied to the electrodes, wherein the controller controls electrical stimulation that is applied to the vagus nerves in both ears such that a difference between a first value of E for a first ear and a second value of E for a second ear becomes 5,000 or more, wherein E is expressed by the following [Equation 1], $$E = V^2 \times F \times PW \qquad \text{[Equation 1]}$$

(where, as units in the equation 1, the intensity is V, the frequency is Hz, and the pulse width is μs), wherein a difference of the frequency (F) is 5 Hz or more, or wherein the intensity (V) of electrical stimulation applied to an ear is larger by 5% or more than smaller intensity (V) at the other ear.

* * * * *